United States Patent [19]
Albers et al.

[11] 4,110,539
[45] Aug. 29, 1978

[54] PROCESS FOR THE PREPARATION OF 2,2,4-TRIMETHYL-1,3-PENTANEDIOL DIISOBUTYRATE

[75] Inventors: Kenneth H. Albers, Houston; Howard N. Wright, Jr., Longview, both of Tex.

[73] Assignee: Eastman Kodak Company, Rochester, N.Y.

[21] Appl. No.: 815,135

[22] Filed: Jul. 13, 1977

[51] Int. Cl.$^2$ ............................................. C07C 67/24
[52] U.S. Cl. .................................. 560/240; 260/340.7; 260/601 R
[58] Field of Search ........................... 260/496, 601 R; 560/240

[56] References Cited

U.S. PATENT DOCUMENTS

| 2,607,800 | 8/1952 | Arundale | 260/496 |
| 3,367,966 | 2/1968 | Knopf et al. | 560/240 |

OTHER PUBLICATIONS

Arundale et al., Chem. Reviews, vol. 51, No. 3, Dec. 1952, pp. 519–528.

Primary Examiner—Vivian Garner
Attorney, Agent, or Firm—Edward R. Weber; Daniel B. Reece, III

[57] ABSTRACT

This invention describes a process for the synthesis of 2,2,4-trimethyl-1,3-pentanediol diisobutyrate by the acid catalyzed cleavage and esterification of 2,4-diisopropyl-5,5-dimethylmetadioxane.

11 Claims, No Drawings

PROCESS FOR THE PREPARATION OF 2,2,4-TRIMETHYL-1,3-PENTANEDIOL DIISOBUTYRATE

This invention describes a process for the synthesis of 2,2,4-trimethyl-1,3-pentanediol diisobutyrate by the acid catalyzed cleavage and esterification of 2,4-diisopropyl-5,5-dimethylmetadioxane.

2,4-Diisopropyl-5,5-dimethylmetadioxane occurs as a byproduct in the commercial production of 2,2,4-trimethyl-1,3-pentanediol monoisobutyrate. At present, there are no known commercial uses for 2,4-diisopropyl-5,5-dimethylmetadioxane.

It is theefore an object of the present invention to provide a simple, efficient process for converting 2,4-diisopropyl-5,5-dimethylmetadioxane into useful products.

It is a further object of this invention to provide a process for producing 2,2,4-trimethyl-1,3-pentanediol diisobutyrate from 2,4-diisopropyl-5,5-dimethylmetadioxane.

These and other objects of the invention will become apparent from the following specification and claims.

According to the process of the instant invention, 2,4-diisopropyl-5,5-dimethylmetadioxane, isobutyric acid, and a strong acid catalyst such as paratoluenesulfonic acid, sulfuric acid, or phosphoric acid, are heated at a temperature from about 80° to 200° C. for from 1.5 to 32 hours. A preferred set of operating conditions is a temperature of from about 105° to about 140° C. and a time of from about 5 to about 15 hours. Good results are obtained when the ratio of 2,4-diisopropyl-5,5-dimethylmetadioxane to isobutyric acid is from about 0.1:1 to about 0.5:1 and preferably about 0.2:1 to about 0.4:1. Products of the reaction are 2,2,4-trimethyl-1,3-pentanediol diisobutyrate and isobutyraldehyde. Water may be additionally added to the process, but its presence is not necessary and in some instances is undesirable, as it makes the system more corrosive. Both isobutyraldehyde and 2,2,4-trimethyl-1,3-pentanediol diisobutyrate are commercial products, for which those skilled in the art are aware of many uses.

E. Arundale and L. A. Mikeska in *Chemical Reviews*, 51, 501–555 (especially pages 524–525), teach that cyclic acetals hydrolyze and that the glycol then dehydrates to form a diene. It is also known that 2,4-diisopropyl-5,5-dimethylmetadioxane can be converted into 2,5-dimethyl-2,4-hexadiene in the presence of isobutyric acid and strog acid such as paratoluenesulfonic acid.

It was therefore quite surprising that 2,4-diisopropyl-5,5-dimethylmetadioxane could be reacted to produce isobutyraldehyde and 2,2,4-trimethyl-1,3-pentanediol diisobutyrate under relatively mild conditions and with good yields. It is hypothesized that the reaction proceeds according to the following formula, although applicants do not wish to be bound by this theory.

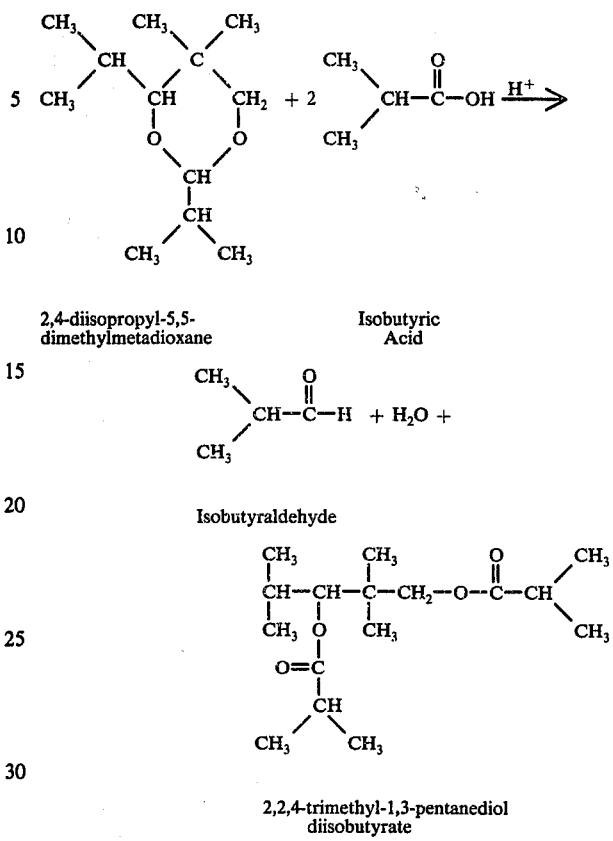

2,4-diisopropyl-5,5-dimethylmetadioxane + Isobutyric Acid $\xrightarrow{H^+}$

Isobutyraldehyde + $H_2O$ +

2,2,4-trimethyl-1,3-pentanediol diisobutyrate 2,4-diisopropyl-5,5-dimethylmetadioxane is relatively inert to hydrolysis under the usual conditions as illustrated by Examples 4 and 5. Hydrolysis with 10 percent water at 109° C. using p-toluenesulfonic acid catalysis is very corrosive. Under the preferred conditions of the instant invention most water formed during the reaction is distilled overhead with the isobutyraldehyde produced by the reaction. Corrosion is significantly reduced when water in the reaction base is maintained at a low level (less than 1%). The 2,4-diisopropyl-5,5-dimethylmetadioxane is inert to isobutyric acid at 169° C. for 7.5 hours reflux (Example 6) and produces only small amounts of 2,2,4-trimethyl-1,3-pentanediol diisobutyrate in the presence of 0.25 percent p-toluenesulfonic acid at 200° C. reflux for 10 hours (Example 9). 2,2,4-Trimethyl-1,3-pentanediol diisobutyrate cracks (Example 7) at 200° C. to produce isobutyric acid and 2,5-dimethyl-2,4-hexadiene as the principal products. It was unobvious, therefore, that the reaction of 2,4-diisopropyl-5,5-dimethylmetadioxane with isobutyric acid with strong acid catalysis in the preferred reaction temperature range would produce isobutyraldehyde and 2,2,4-trimethyl-1,3-pentanediol diisobutyrate in yields of up to about 90 percent.

Various strong acid catalysts such as sulfuric acid, phosphoric acid, and p-toluenesulfonic acid have been found to be useful as catalysts. Those skilled in the art will understand that additional catalysts, such as mixed sulfonic acids, may also be used and that only a catalytic amount is required. Good results have been obtained with catalyst concentrations of from about 0.2 to about 4 percent by weight of the total reaction mass. A preferred range of catalyst concentration is from about 0.5 to about 2 percent. Likewise, if desired for purposes of temperature control, an inert solvent may be used, but this is not necessary and is not a critical feature of the invention.

The process of the instant invention is illustrated in greater detail by the following examples. It is understood that these examples are not intended to limit the scope of the invention, and obvious modifications will occur to those skilled in the art.

EXAMPLE 1

This example illustrates a preferred process for the synthesis of 2,2,4-trimethyl-1,3-pentanediol diisobutyrate from 2,4-diisopropyl-5,5-dimethylmetadioxane. A 1000 milliliter round bottom flask is charged with 280 grams (1.33 moles of 95 percent purity) of 2,4-diisopropyl-5,5-dimethylmetadioxane, 370 grams (4.20 moles) of isobutyric acid, and 6.8 grams of p-toluenesulfonic acid. The reaction mixture is heated in the base of a 30 plate one inch diameter Oldershaw column with a reflux ratio of 3.3/1. The reaction solution is heated at 120° C. for 7 hours. The reaction solution is analyzed on a gas chromatograph using a 6 foot by ⅛ inch 10 percent SP-2300 column followed by a 10 foot by ⅛ inch 10 percent SE-30 column. The program is run from 70° C. to 250° C. at 15° C. per minute with an upper limit hold for a total program time of 1000 seconds. Analysis shows a 92 percent yield to 2,2,4-trimethyl-1,3-pentanediol diisobutyrate based upon a 38 percent conversion of the 2,4-diisopropyl-5,5-dimethylmetadioxane.

EXAMPLE 2

This example illustrates the process in which a higher reaction temperature and smaller concentration of isobutyric acid are used. A 1000 milliliter round bottom flask is charged with 420 grams (2.00 moles of 95 percent purity) of 2,4-diisopropyl-5,5-dimethylmetadioxane, 370 grams (4.20 moles) of isobutyric acid, and 7.9 grams of p-toluenesulfonic acid. The reaction mixture is heated to 150° C. and held at 150° C. for 6 hours. Isobutyraldehyde, 61.8 grams, is collected overhead. Analysis of the base by the technique of Example 1 gives a 55 percent conversion of the acetal and a 73 percent yield of 2,2,4-trimethyl-1,3-pentanediol diisobutyrate.

EXAMPLE 3

This example illustrates the process in a continuous unit in which water is added to the reaction medium. The continuous hydrolysis reactor comprises a 3 foot column packed with Penn State packing and fitted with an overhead vapor takeoff, overhead decanter, and a base heater. The base heater flask is a 5 liter, five neck flask fitted with a thermowell, water feed line, organic feed line, and base overflow line. Feeds to the hydrolysis reactor are mixed in the following ratios.

| | p-Toluene-sulfonic Acid | Water | Iso-butyric Acid | Acetal* | Recycle Column Overhead |
|---|---|---|---|---|---|
| Initial Feeds Organic | | | | 1000 ml. | 1000 ml. |
| Water | 62.4 g. | 700 ml. | | | |
| Recycle Feed | | | 300 ml. | 700 ml. | 1000 ml. |

*2,4-diisopropyl-5,5-dimethylmetadioxane

The base flask is charged with 3 liters of initial organic feed, 300 milliliters of water, and 62.4 grams of p-toluenesulfonic acid catalyst. The column is operated batchwise overnight to produce 340 milliliters of an isobutyraldehyde cut and 205 milliliters of water layer from the overhead decanter. Initial organic feed mixture is then fed continuously at 125 milliliters per hour and initial water feed mixture at 30 milliliters per hour. Isobutyraldehyde is distilled overhead as it forms. Water is drained from the overhead decanter when the base temperature is below 108° C. Reaction mixture is pumped from the base heater to maintain the base level at 3000 milliliters.

The reactor base overflow forms two layers on cooling. Each day this material is decanted and the organic layer is extracted with three 200 milliliter portions of water layer from the overhead decanter. Catalyst concentration in the organic layer is reduced from 4600 ppm. p-toluenesulfonic acid to 260 ppm. after the first extraction and to less than 6 ppm. after the second and third extractions. The extractor water layer is recycled to the hydrolysis column base heater after the second day.

Conversion of the 2,4-diisopropyl-5,5-dimethylmetadioxane averages 72 mole percent per pass. The reactor residence time averages 23.6 hours. Overall yields are 98 mole percent 2,4-diisopropyl-5,5-dimethylmetadioxane to isobutyraldehyde and 93 mole percent to a mixture of 2,2,4-trimethyl-1,3-pentanediol mono- and diisobutyrate.

EXAMPLES 4–17

Examples 4 and 5 demonstrate that 2,4-diisopropyl-5,5-dimethylmetadioxane is not susceptable to hydrolysis. Example 6 illustrates that 2,4-diisopropyl-5,5-dimethylmetadioxane is unreactive in the presence of isobutyric acid. Example 7 is a reference run to show that 2,2,4-trimethyl-1,3-pentanediol diisobutyrate will decompose if heated at or above the upper temperature limit in the presence of p-toluenesulfonic acid.

Examples 8 through 18 demonstrate the range of catalyst concentrations and reaction temperatures and illustrate the use of several catalysts. Preferred catalysts include p-toluenesulfonic acid and Amberlyst 15 ion exchange resin manufactured by Rohm and Haas Company.

Table 1

| Example | Catalyst | % Catalyst | Acetal/Acid* Mole Ratio | Other Reactants | Reaction Temp, °C. | Time, hr. | % Conversion | Material Accountability, % | Diester** Yield % |
|---|---|---|---|---|---|---|---|---|---|
| 4 | $H_3PO_4$ | 2.3 | (1) | 67% $H_2O$ | 102 | 7 | <1 | 95 | 0 |
| 5 | $H_2SO_4$ | 2.5 | (1) | 22% $H_2O$ | 95 | 11 | 9 | 96 | |
| 6 | — | — | 0.5 | — | 169 | 7.5 | No Reaction | | 0 |
| 7 | p-TSA*** | 1 | (2) | 99% Diester | 200 | 10 | >98 | 99.6 | — |
| 8 | p-TSA | 2 | 0.33 | — | 80 | 32 | 24 | 98.2 | 82 |
| 9 | p-TSA | 0.25 | 2.05 | — | 200 | 10 | 33 | 97.2 | 8 |
| 10 | p-TSA | 1 | 0.32 | — | 140 | 15 | 80 | 96.8 | 80 |

Table 1-continued

| Example | Catalyst | % Catalyst | Acetal/Acid* Mole Ratio | Other Reactants | Reaction Temp, °C. | Reaction Time, hr. | % Conversion | Material Accountability, % | Diester** Yield % |
|---|---|---|---|---|---|---|---|---|---|
| 11 | p-TSA | 1 | 0.19 | — | 130 | 7 | 49 | 99.8 | 90 |
| 12 | $H_2SO_4$ | 1.9 | 0.50 | 10% $H_2O$ | 109 | 16 | 89 | — | 54 |
| 13 | $H_3PO_4$ | 1.9 | 0.50 | 10% $H_2O$ | 109 | 31 | 64 | — | 22 |
| 14 | A-15**** | 4 | 0.50 | 3% $H_2O$ | 114 | 31 | 71 | — | 23 |
| 15 | $NH_4Cl$ | 1.7 | 0.50 | 3% $H_2O$ | 135 | 25.5 | 60 | — | 33 |
| 16 | p-TSA | 1 | 0.33 | — | 140 | 1.5 | 36 | 98 | 71 |
| 17 | p-TSA | 2 | 0.32 | — | 120 | 3 | 28 | 95 | 76 |
| 18 | A-15 | 3 | 0.21 | 3% $H_2O$ | 115 | 25 | 62 | 98 | 85 |

*Acetal/acid = 2,4-diisopropyl-5,5-dimethylmetadioxane/isobutyric acid
**Diester = 2,2,4-Trimethyl-1,3-Pentanediol Diisobutyrate
***p-TSA = p-Toluenesulfonic Acid
****A-15 = Amberlyst 15 Ion Exchange Resin
(1) = No Acid Introduced
(2) = No Acetal or Acid Introduced The invention has been described in detail with particular reference to preferred embodiments thereof, but it will be understood that variations and modifications can be effected within the spirit and scope of the invention as described hereinabove and in the appended claims.

We claim:

1. A process for the synthesis of 2,2,4-trimethyl-1,3-pentanediol diisobutyrate wherein a mixture of 2,4-diisopropyl-5,5-dimethylmetadioxane and isobutyric acid is reacted in the presence of a strong acid catalyst at a temperature of from about 80° C. to about 200° C.

2. A process according to claim 1 wherein the molar ratio of 2,4-diisopropyl-5,5-dimethylmetadioxane to isobutyric acid is from about 0.1:1 to about 0.5:1.

3. A process according to claim 2 wherein the molar ratio of 2,4-diisopropyl-5,5-dimethylmetadioxane to isobutyric acid is from about 0.2:1 to about 0.4:1.

4. A process according to claim 1 wherein the reaction is conducted at a temperature of from about 105° to about 140° C.

5. A process according to claim 1 wherein the strong acid catalyst is present to the extent of from about 0.2 to about 4 percent by weight of the total reaction mixture.

6. A process according to claim 5 wherein the strong acid catalyst is present to the extent of from about 0.5 to about 2 percent by weight of the total reaction mixture.

7. A process according to claim 1 wherein the strong acid catalyst is selected from the group consisting of sulfuric acid, phosphoric acid, p-toluenesulfonic acid, and mixtures thereof.

8. A process according to claim 1 wherein the strong acid catalyst is p-toluenesulfonic acid.

9. A process according to claim 1 wherein the materials are reacted for from about 1.5 to about 32 hours.

10. A process according to claim 9 wherein the materials are reacted for from about 5 to about 15 hours.

11. A process according to claim 1 wherein the reaction is conducted in the presence of from about 0 to about 15% of added water.

* * * * *